(12) United States Patent
Prior et al.

(10) Patent No.: US 12,343,043 B2
(45) Date of Patent: *Jul. 1, 2025

(54) ROBOTICALLY AND MANUALLY OPERABLE UTERINE MANIPULATORS

(71) Applicant: Covidien LP, Mansfield, MA (US)

(72) Inventors: Scott J. Prior, Branford, CT (US); Zachary Traina, Verona, NJ (US); Arvind Rajagopalan Mohan, Dracut, MA (US); Nikolai D. Begg, Wellesley, MA (US); Kevin R. Slisz, Elkton, FL (US)

(73) Assignee: Coviden LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/483,807

(22) Filed: Oct. 10, 2023

(65) Prior Publication Data

US 2024/0032967 A1    Feb. 1, 2024

Related U.S. Application Data

(63) Continuation of application No. 17/172,222, filed on Feb. 10, 2021, now Pat. No. 11,806,048.
(Continued)

(51) Int. Cl.
*A61B 17/00* (2006.01)
*A61B 17/42* (2006.01)
(Continued)

(52) U.S. Cl.
CPC .......... *A61B 17/4241* (2013.01); *A61B 34/35* (2016.02); *A61B 34/71* (2016.02);
(Continued)

(58) Field of Classification Search
CPC ............ A61B 17/2841; A61B 17/2909; A61B 17/4241; A61B 2017/0042;
(Continued)

(56) References Cited

U.S. PATENT DOCUMENTS 3,938,521 A    2/1976    Ritota et al.
5,643,285 A    7/1997    Rowden et al.
(Continued)

FOREIGN PATENT DOCUMENTS

WO    2011002215 A2    1/2011

OTHER PUBLICATIONS

International Search Report and Written Opinion issued in corresponding application PCT/US2021/019539 dated Jun. 9, 2021 (15 pages).

*Primary Examiner* — Kelly J Bekker
*Assistant Examiner* — Lindsey R. Rivers
(74) *Attorney, Agent, or Firm* — Carter, DeLuca & Farrell LLP (57) ABSTRACT

A uterine manipulator includes a housing configured to be coupled to an instrument drive unit of a robotic system, a shaft extending distally from the housing, a tip hub pivotably coupled to a distal end portion of the shaft, an articulation disposed within the housing, and a handle operably coupled to either the housing or the shaft. The articulation assembly is configured to pivot the tip hub relative to the shaft and includes a drive cable operably coupled to the tip hub. The articulation assembly is actuatable manually by a user and robotically by the robotic system to pivot the tip hub relative to the shaft. The handle is configured to be manually gripped by a user for manual use of the uterine manipulator.

11 Claims, 9 Drawing Sheets

Related U.S. Application Data (60) Provisional application No. 62/987,393, filed on Mar. 10, 2020.

(51) Int. Cl.
  *A61B 34/00* (2016.01)
  *A61B 34/35* (2016.01)
  *A61B 17/12* (2006.01)

(52) U.S. Cl.
  CPC ............ *A61B 2017/00424* (2013.01); *A61B 2017/0046* (2013.01); *A61B 2017/00477* (2013.01)

(58) Field of Classification Search
  CPC .. A61B 2017/00424; A61B 2017/0046; A61B 2017/00477; A61B 34/35; A61B 34/71
  See application file for complete search history.

(56) References Cited

U.S. PATENT DOCUMENTS

| | | |
|---|---|---|
| 5,746,750 A | 5/1998 | Prestel et al. |
| 5,840,077 A | 11/1998 | Rowden et al. |
| 7,717,312 B2 | 5/2010 | Beetel |
| 8,025,670 B2 | 9/2011 | Sharp et al. |
| 8,192,444 B2 | 6/2012 | Dycus |
| 8,292,901 B2 | 10/2012 | Auerbach et al. |
| 8,475,469 B2 | 7/2013 | Walter et al. |
| 8,603,105 B2 | 12/2013 | Sauer |
| 8,696,563 B2 | 4/2014 | Williams et al. |
| 8,740,916 B2 | 6/2014 | Blair et al. |
| 8,747,413 B2 | 6/2014 | Dycus |
| 9,011,433 B2 | 4/2015 | Batchelor et al. |
| 9,554,827 B2 * | 1/2017 | Omori ................ A61B 17/4241 |
| 11,806,048 B2 | 11/2023 | Prior et al. |
| 2010/0041945 A1 | 2/2010 | Isbell, Jr. |
| 2011/0174099 A1 | 7/2011 | Ross et al. |
| 2011/0295242 A1 * | 12/2011 | Spivey ............. A61B 17/07207 606/1 |
| 2013/0023896 A1 | 1/2013 | Quimby |
| 2013/0138115 A1 | 5/2013 | Seckin |
| 2014/0052018 A1 | 2/2014 | Hawkins |
| 2014/0052144 A1 | 2/2014 | Singh et al. |
| 2014/0257322 A1 | 9/2014 | Batchelor et al. |
| 2014/0288486 A1 | 9/2014 | Hart et al. |
| 2014/0330285 A1 | 11/2014 | Rosenblatt et al. |
| 2014/0358158 A1 | 12/2014 | Einarsson |
| 2015/0005780 A1 | 1/2015 | Einarsson |
| 2015/0127016 A1 | 5/2015 | Sauer |
| 2015/0133923 A1 | 5/2015 | Batchelor et al. |
| 2015/0148812 A1 | 5/2015 | Ahluwalia |
| 2015/0272619 A1 | 10/2015 | Zisow |
| 2015/0297254 A1 | 10/2015 | Sullivan et al. |
| 2016/0113732 A1 | 4/2016 | Steege et al. |
| 2016/0302783 A1 | 10/2016 | Greenberg et al. |
| 2019/0008600 A1 | 1/2019 | Pedros et al. |
| 2019/0099227 A1 | 4/2019 | Rockrohr |
| 2020/0060516 A1 | 2/2020 | Baez, Jr. |
| 2020/0237454 A1 | 7/2020 | Anglese |
| 2020/0253676 A1 | 8/2020 | Traina |
| 2020/0315727 A1 | 10/2020 | Zemlok et al. |

\* cited by examiner

ROBOTICALLY AND MANUALLY OPERABLE UTERINE MANIPULATORS

CROSS-REFERENCE TO RELATED APPLICATIONS

This application is a continuation of U.S. application Ser. No. 17/172,222 entitled "ROBOTICALLY AND MANUALLY OPERABLE UTERINE MANIPULATORS" filed Feb. 10, 2021, which claims priority from U.S. Provisional Application Ser. No. 62/987,393, filed Mar. 10, 2020, the entire contents of both of which being incorporated by reference herein.

FIELD

The present disclosure is generally related to surgical instruments. More specifically, the present disclosure relates to a surgical instrument, such as, for example, a uterine manipulator that is both manually operable by a user and robotically operable by a robotic surgical system.

BACKGROUND

Uterine manipulators are medical instruments used for manipulating (e.g., moving or repositioning) a patient's uterus during medical procedures. Such procedures include laparoscopic gynecologic surgery, e.g., total laparoscopic hysterectomy (TLH) surgery. Uterine manipulators typically include a proximal portion that remains external to the patient's body during use and a distal portion that is inserted into the patient's body. The proximal portion typically provides for manipulation of the instrument during use. The distal portion often includes a tip sized to be inserted into and/or engage a uterus. The distal portion of the instrument is advanced through the vaginal cavity and cervix and into the uterus. With the distal portion inserted within a uterus, the uterus can be manipulated through user controlled movements of the proximal portion. Following completion of a procedure, the instrument may be removed from the patient's body via the vaginal cavity.

SUMMARY

In one aspect of the present disclosure, a uterine manipulator is provided and includes a housing configured to be coupled to an instrument drive unit of a robotic system, a shaft extending distally from the housing, a tip hub pivotably coupled to a distal end portion of the shaft, an articulation assembly disposed within the housing, and a handle operably coupled to either the housing or the shaft. The articulation assembly is configured to pivot the tip hub relative to the shaft and includes a drive cable operably coupled to the tip hub. The articulation assembly is actuatable manually by a user and robotically by the robotic system to pivot the tip hub relative to the shaft. The handle is configured to be manually gripped by a user for manual use of the uterine manipulator.

In aspects, the articulation assembly includes a first driven member rotationally supported in the housing and having a proximal end portion configured to be operably coupled to a first drive member of the instrument drive unit and a first nut threadedly coupled to the first driven member such that the first nut translates along the first driven member upon rotation of the first driven member. A proximal end portion of the drive cable is operably coupled to the first nut and a distal end portion of the drive cable is operably coupled to the tip hub such that the drive cable longitudinally translates with the first nut and relative to the first driven member in response to a rotation of the first driven member to articulate the tip hub relative to the shaft.

In aspects, the articulation assembly includes a second driven member rotationally supported in the housing and having a proximal end portion configured to be operably coupled to a second drive member of the instrument drive unit, a second nut threadedly coupled to the second driven member such that the second nut translates along the second driven member upon rotation of the second driven member, and a second drive cable coupled to the second nut. The second drive cable has a proximal end portion operably coupled to the second nut and a distal end portion coupled to the tip hub. The distal end portion of the drive cable is coupled to a first side of the tip hub and the distal end portion of the second drive cable is coupled to a second side of the tip hub.

In aspects, the uterine manipulator includes a rotatable collar operably coupled to a distal end portion of the first driven member such that a rotation of the collar rotates the first driven member. The collar may have a plurality of gear teeth extending from an inner periphery thereof, and the distal end portion of the first driven member has a gear in meshing engagement with the plurality of gear teeth of the collar.

In aspects, the first driven member is parallel with and offset from a longitudinal axis defined by the shaft.

In aspects, the handle extends outward from a proximal portion of the housing and is permanently coupled to the housing.

In aspects, the handle is removably couplable to a proximal portion of the housing and includes a coupling member for releasably coupling the handle to the housing and a window opening defined therethrough for permitting the articulation assembly to couple to the instrument drive unit of the robotic system when the handle is coupled to the housing.

In aspects, the handle is operably coupled to the housing via a hinge as is movable between an unfolded configuration, where the handle extends substantially perpendicular relative to a surface of the housing, and a folded configuration, where the handle extends substantially parallel along the surface of the housing. The housing may define a recess configured to receive the handle in the folded configuration.

In aspects, the shaft is detachable from the housing and the handle is operably coupled to the shaft.

In aspects, a distal portion of the shaft is curved. Additionally, or alternatively, the shaft may define an internal lumen extending along a length of the shaft.

In another aspect of the disclosure, a uterine manipulator is provided and includes a housing configured to be coupled to an instrument drive unit of a robotic system, a shaft extending distally from the housing, a tip hub pivotably coupled to a distal end portion of the shaft, an articulation assembly disposed within the housing, and a handle pivotably coupled to the housing. The articulation assembly is configured to pivot the tip hub relative to the shaft and includes a drive cable operably coupled to the tip hub. The articulation assembly is actuatable manually by a user and robotically by the robotic system to pivot the tip hub relative to the shaft. The handle is pivotably coupled to the housing via a hinge and is movable between an unfolded configuration, where the handle extends substantially perpendicular relative to a surface of the housing, and a folded configuration, where the handle extends substantially parallel along the surface of the housing. The handle is configured to be manually gripped by a user for manual use of the uterine manipulator.

In aspects, the uterine manipulator includes a rotatable collar operably coupled to the articulation assembly and configured to be manually rotated to pivot the tip hub relative to the shaft.

In aspects, the housing defines a recess and the handle is configured to be positioned within the recess when in the folded configuration.

In aspects, the articulation assembly includes a first driven member rotationally supported in the housing and having a proximal end portion configured to be operably coupled to a first drive member of the instrument drive unit and a first nut threadedly coupled to the first driven member such that the first nut translates along the first driven member upon rotation of the first driven member. A proximal end portion of the drive cable is operably coupled to the first nut and a distal end portion of the drive cable is operably coupled to the tip hub such that the drive cable longitudinally translates with the first nut and relative to the first driven member in response to a rotation of the first driven member to articulate the tip hub relative to the shaft.

In aspects, the articulation assembly includes a second driven member rotationally supported in the housing and having a proximal end portion configured to be operably coupled to a second drive member of the instrument drive unit, a second nut threadedly coupled to the second driven member such that the second nut translates along the second driven member upon rotation of the second driven member, and a second drive cable coupled to the second nut. The second drive cable has a proximal end portion operably coupled to the second nut and a distal end portion coupled to the tip hub. The distal end portion of the drive cable is coupled to a first side of the tip hub and the distal end portion of the second drive cable is coupled to a second side of the tip hub.

In yet another aspect of the disclosure, a uterine manipulator is provided and includes a housing configured to be coupled to an instrument drive unit of a robotic system, a shaft extending distally from the housing, a tip hub pivotably coupled to a distal end portion of the shaft, an articulation assembly disposed within the housing, and a handle removably coupled to the housing. The articulation assembly is configured to pivot the tip hub relative to the shaft and includes a drive cable operably coupled to the tip hub. The articulation assembly is actuatable manually by a user and robotically by the robotic system to pivot the tip hub relative to the shaft. The handle removably coupled to the housing via a coupling member and is configured to be manually gripped by a user for manual use of the uterine manipulator.

In aspects, the uterine manipulator includes a rotatable collar operably coupled to the articulation assembly and configured to be manually rotated to pivot the tip hub relative to the shaft.

In aspects, the handle defines a window opening for permitting the articulation assembly to couple to the instrument drive unit of the robotic system when the handle is coupled to the housing.

As used herein, the term "distal" refers to that portion of the described component which is farthest from the user, while the term "proximal" refers to that portion of the described component which is closest to the user.

As used herein, the terms "parallel" and "perpendicular" are understood to include relative configurations that are substantially parallel or perpendicular up to about + or −10 degrees from true parallel or perpendicular. Likewise, the terms "about", "substantially" and similar terms account for variation of up to about + or −10 percent.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the present disclosure will now be described in detail with reference to the drawings, in which like reference numerals designate identical or corresponding elements in each of the several views. In the following description, well-known functions or constructions are not described in detail to avoid obscuring the present disclosure in unnecessary detail.

The present disclosure provides surgical instruments, e.g., uterine manipulators, configured to facilitate transcervical evaluation. Although the aspects and features of the present disclosure are detailed below with respect to uterine manipulators, it is contemplated that the aspects and features of the present disclosure may likewise be utilized with any other suitable surgical instruments. Further, although the uterine manipulators of the present disclosure are detailed hereinbelow for the purpose of facilitating transcervical evaluation, the uterine manipulators of the present disclosure are also configured to facilitate performance of other surgical tasks typically accomplished at least in part using uterine manipulators, e.g., colpotomy procedures and/or other tasks associated with a hysterectomies; diagnostic procedures; tubal ligations; treatment of endometriosis; removal of adhesions, fibroids, or cysts; etc.

FIGS. 1A-1B, FIGS. 2A-2B, FIGS. 3A-3B, and FIGS. 4A-4B illustrate uterine manipulators 100, 200, 300, and 400, respectively, which are collectively referred to herein as the uterine manipulator 10 (FIGS. 5-10). The uterine manipulator 10 is both robotically operable by a robotic surgical system 1 and manually operable by a user. More specifically, as described in greater detail below, the uterine manipulator 10 includes components for manually operating and manipulating the uterine manipulator 10 and components for coupling the uterine manipulator to a robotic surgical system 1 for robotically operating and manipulating the uterine manipulator 10 and components thereof. The uterine manipulator 10 generally includes a housing 36, an articulation assembly 38 (FIGS. 7-8) disposed within the housing 36, a shaft 40 extending distally from the housing 36, a tip hub 42 pivotably coupled to a distal end portion 44 of the shaft 40, a tip member 34 attached to the tip hub 42, and a cervical cup 46 positionable about the shaft 40. The articulation assembly 38 controls components of the uterine manipulator for example the pivoting of tip hub 42, is manually operable, for example via a user-controlled rotatable collar 58, and robotically operable when the uterine manipulator 10 is coupled to a robotic surgical system 1. The shaft 40 may be straight or curved at portions along its length.

Figures 1A, 1B:
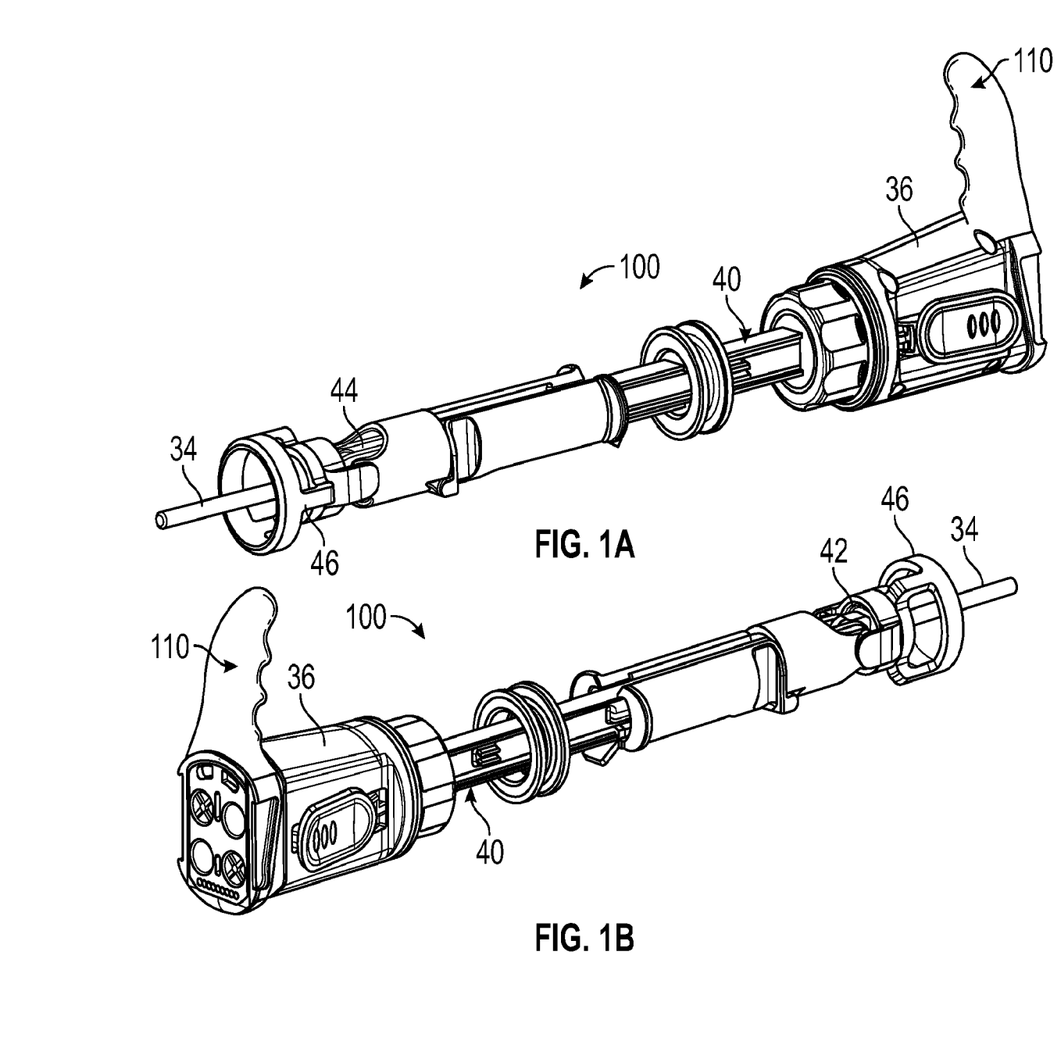
FIG. 1A is a side, front, perspective view illustrating a uterine manipulator in accordance with the present disclosure.
FIG. 1B is a side, rear, perspective view illustrating the uterine manipulator of FIG. 1A.

With reference to FIGS. 1A-1B, uterine manipulator 100 includes a handle 110 extending outwardly from a surface of the housing 36. The handle 110 of uterine manipulator 100 may be fixedly coupled to the housing 36, or may be formed as a single unitary component with the housing 36. The handle 110 is configured to be manually gripped by a user for manipulating the entire uterine manipulator 100 or only select portions thereof (e.g., the tip hub 42). The handle 110 may extend perpendicularly relative to a longitudinal axis defined by the handle 110 or at an angle relative thereto, e.g., between about 45 degrees and 90 degrees. The handle 110 is positioned so as to not interfere with the robotic interface controls accessible from housing 36.

Figure 2A:
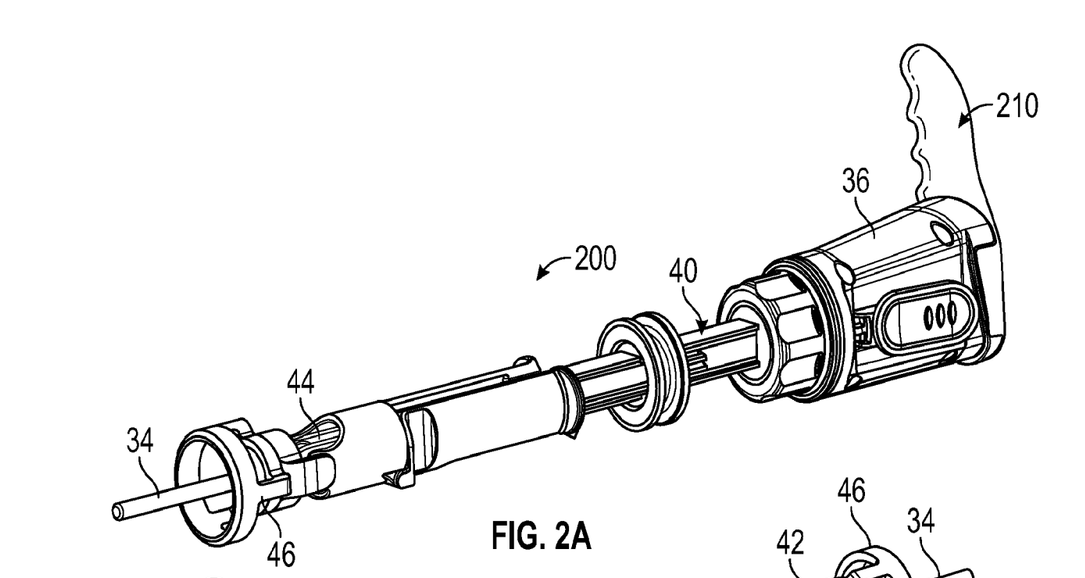
FIG. 2A is a front, side, perspective view illustrating another uterine manipulator in accordance with the present disclosure.
Figure 2B:
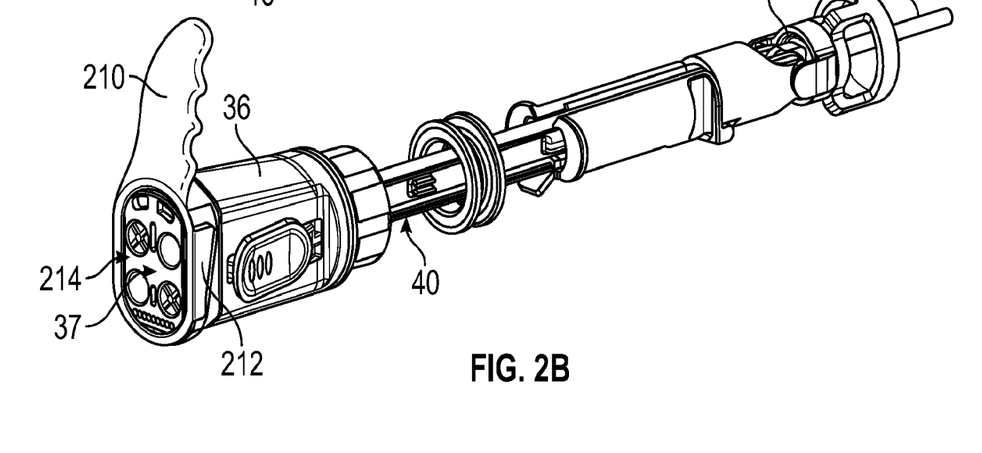
FIG. 2B is a rear, side, perspective view illustrating the uterine manipulator of FIG. 2A.

With reference to FIGS. 2A-2B, uterine manipulator 200 includes a removable handle 210 configured to couple to at least one of the housing 36 or the shaft 40. The handle 210 of uterine manipulator 200 is a separate component from the housing 36 and is configured to be secured to the housing 36, or another portion of the uterine manipulator 200, via a coupling member 212. The handle 210 is configured to be manually gripped by a user for manipulating the uterine manipulator 200 when the handle 210 is coupled to the housing 36.

Coupling member 212 may be a snap-fit engagement mechanism for removably securing the handle 210 to the housing 36 or another portion of the uterine manipulator 200, such as the shaft 40. For example, coupling member 212 may be a protrusion extending from a surface of the handle 210 which is configured to snap-fit to a recess defined on an outer surface of the housing 36, though other engagement configurations are contemplated for releasably securing the handle 210 to the housing 36.

The handle 210 may be removably secured to a proximal portion of the housing 36. To prevent the handle 210 from obstructing an interface region 37 where the uterine manipulator 200 couples to a robotic surgical system 1, the handle 210 may define a window opening 214 which serves to provide access to (or otherwise not obstruct) the robotic interface controls, when such interface controls are located on a proximal end of the housing 36.

Figure 3A:
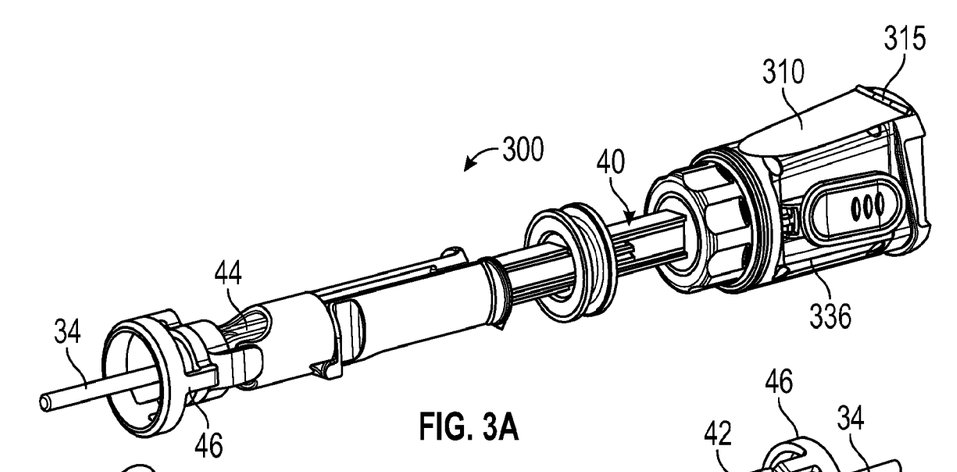
FIG. 3A is a front, side, perspective view illustrating another uterine manipulator in accordance with the present disclosure disposed in a first condition.
Figure 3B:
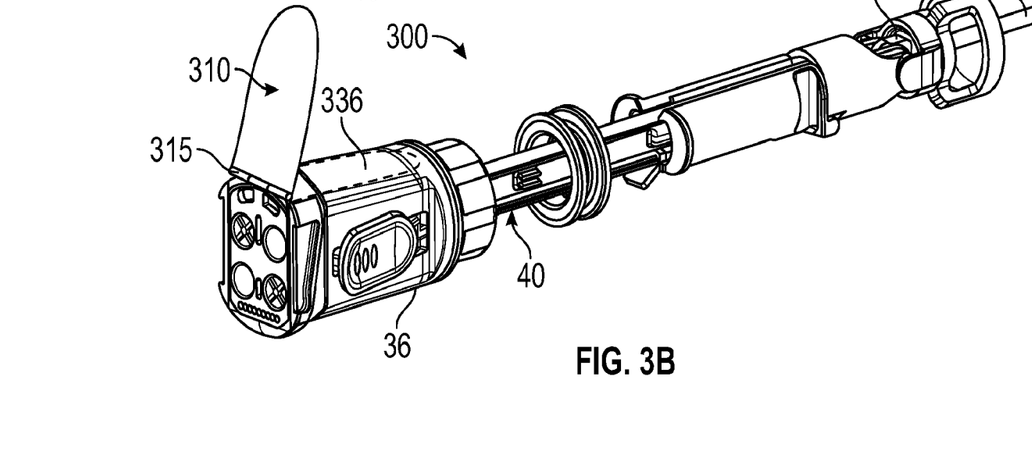
FIG. 3B is a rear, side, perspective view illustrating the uterine manipulator of FIG. 3A disposed in a second condition.

With reference to FIGS. 3A-3B, uterine manipulator 300 includes a housing 36 having a foldable handle 310 configured to pivot relative to the housing 36. The handle 310 of uterine manipulator 300 is coupled to the housing 36, or another portion of the uterine manipulator 300, via a hinge 315 and is configured to transition between a folded configuration and an extended, unfolded configuration. The handle 310 is configured to be manually gripped by a user for manipulating the uterine manipulator 300 when the handle 310 is in the extended, unfolded configuration.

The hinge 315 may be a lockable hinge that enables a user to releasably lock the handle 310 in the folded and/or unfolded configurations. In the extended, unfolded configuration, the handle 310 extends substantially perpendicular relative to a longitudinal axis of the housing 36, outwardly from a surface of the housing 36, or at another suitable angle relative thereto, e.g., between about 45 degrees and 90 degrees. In the folded configuration, the handle 310 rests flat against a surface (for example, a top surface) of the housing 36. The housing 36 may include a recess 336 configured to receive the handle 310 therein when the handle 310 is in the folded configuration. The recess 336 may be defined along an outer surface of the housing 36 and may be shaped and dimensioned to correspond in shape and size of the handle 310 so that the handle 310 does not protrude fully, or partially, from the housing 36 when the handle 310 is in the folded configuration.

Figure 4A:
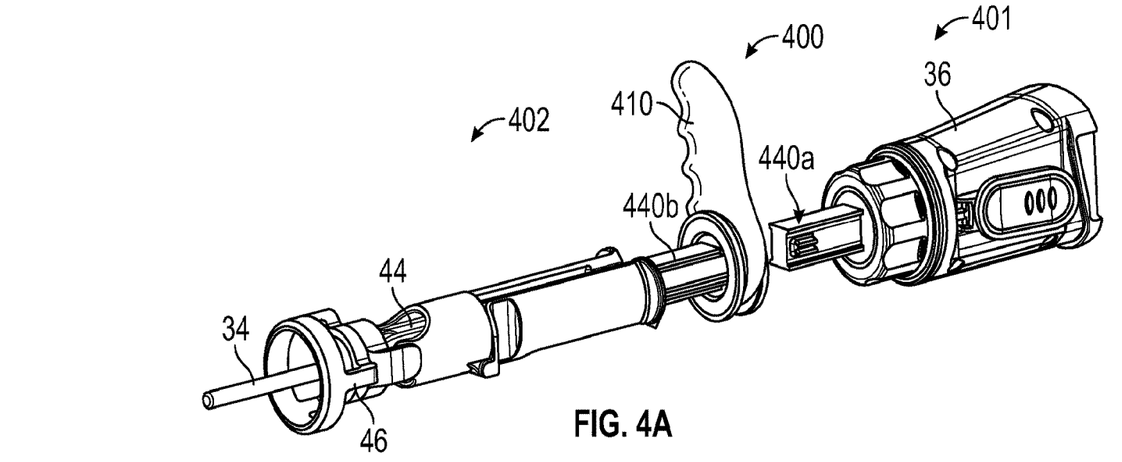
FIG. 4A is a front, side, perspective view illustrating another uterine manipulator in accordance with the present disclosure.
Figure 4B:
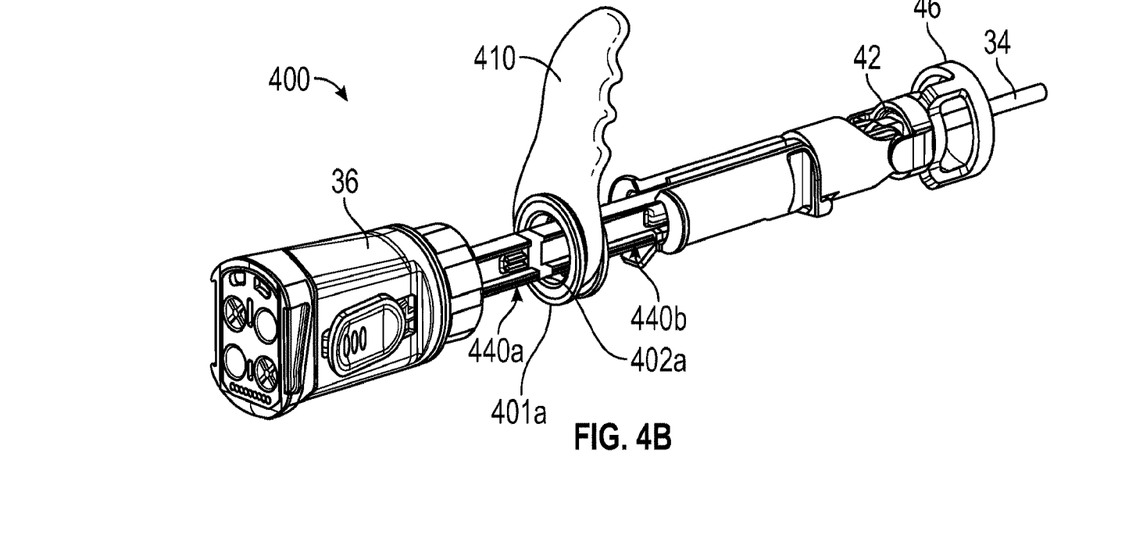
FIG. 4B is a rear, side, perspective view illustrating the uterine manipulator of FIG. 4A.

With reference to FIGS. 4A-4B, uterine manipulator 400 includes a proximal portion 401 separable from a distal portion 402. The proximal portion 401 of the uterine manipulator 400 includes a housing 36 having an articulation assembly 38 (FIGS. 7-8) disposed within the housing 36 and a shaft 440a extending distally from the housing 36. The distal portion 402 of the uterine manipulator 400 includes a shaft 440b configured to couple to the shaft 440a of the proximal portion 401 when the uterine manipulator 400 is used with a robotic surgical system 1. The shaft 440b of the distal portion 402 also includes a handle 410 extending therefrom for manual operation by a user when the uterine manipulator 400 is manually operated and/or not coupled to a robotic surgical system 1. The distal portion 402 of the uterine manipulator 400 also includes a tip hub 42 pivotably coupled to a distal end portion 44 of the shaft 440b, a tip member 34 attached to the tip hub 42, and a cervical cup 46 positionable about the shaft 440b.

The distal portion 402 includes a coupling mechanism 402a which is configured to secure to a corresponding coupling mechanism 401a of the proximal portion 401. Coupling mechanisms 401a, 402a may be any suitable structure for releasably securing the distal portion 402 to the proximal portion 401 of uterine manipulator 400. Additionally, coupling mechanisms 401a, 402a may include means for coupling any drive members, cabling, or fluid lumens that extend from the proximal portion 401 to the distal portion 402.

Any of the above-described handles 110, 210, 310, 410 of uterine manipulators 100, 200, 300, 400 may be operably coupled to the articulation assembly 38, or otherwise coupled to the tip hub 42 (e.g., via an independent drive rod) to articulate (e.g., pivot) the tip hub 42 relative to the shaft 40. For example, an actuation linkage (e.g., a cable, rod, or other suitable link) may extend through shaft 40 and operably couples handle 110, 210, 310, 410 with tip hub 42 to enable pivoting of tip hub 42 relative to shaft 40 in response to pivoting of handle 110, 210, 310, 410 relative to shaft 40 and/or housing 36 (see FIGS. 1A-4B). Other suitable configurations for pivoting tip hub 42 relative to shaft 40 in response to manipulation of handle 110, 210, 310, 410 (or a portion thereof; FIGS. 1A-4B) are also contemplated such as, for example, other mechanical configurations, motor-driven configurations, etc. Further, gearing or other suitable mechanisms may be provided to amplify or attenuate the pivoting of tip hub 42 in response to manipulation of handle 110, 210, 310, 410 (see FIGS. 1A-4B). Handle 110, 210, 310, 410 (see FIGS. 1A-4B) may be pivotable in either direction from an at-rest position relative to shaft 40, e.g., to thereby enable pivoting of tip hub 42 in either direction relative to shaft 40 from its at-rest position. Additionally, or alternatively, each of uterine manipulators 100, 200, 300, 400 (see FIGS. 1A-4B) may include a manually operable rotatable collar 58 (described below) coupled to the articulation assembly 38 to manually operate articulation (e.g., pivoting) of the tip hub 42 relative to the shaft 40.

Figure 5:
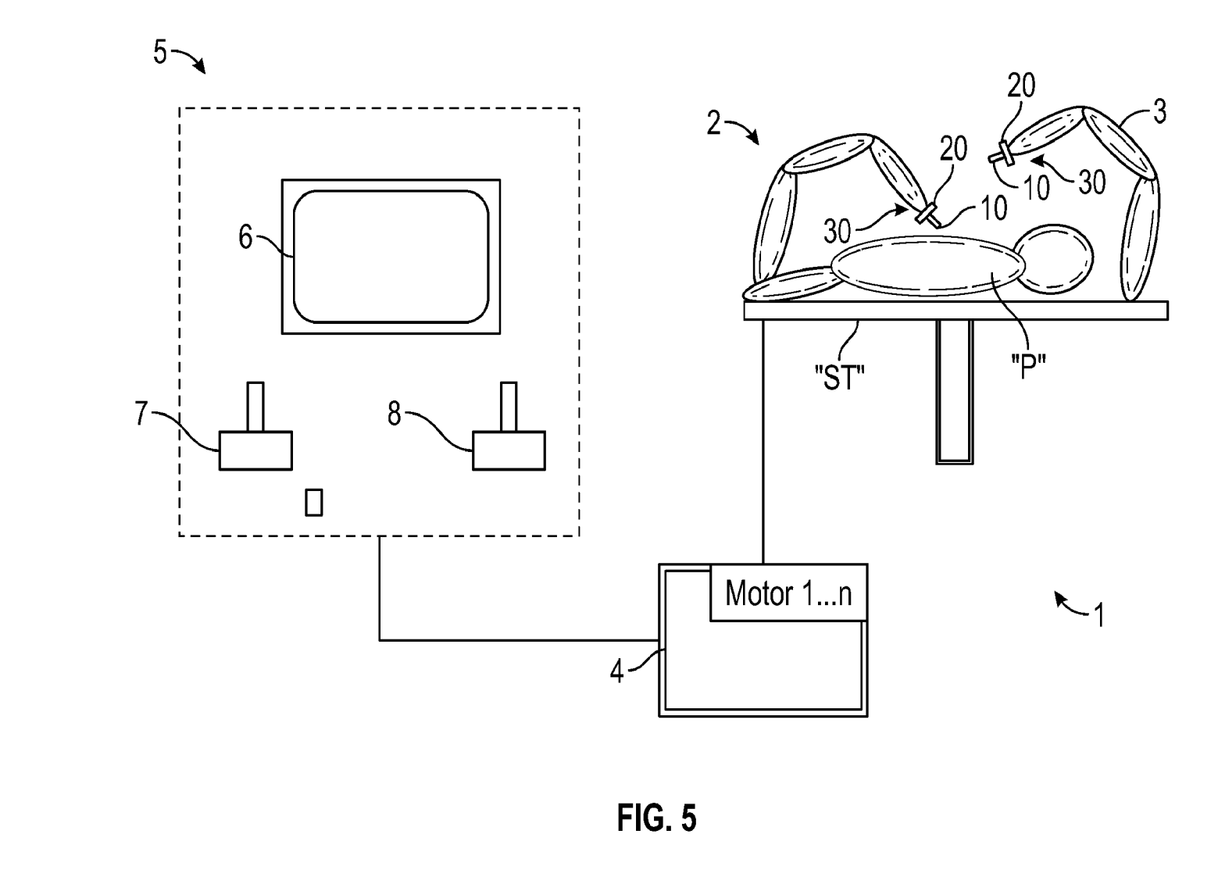
FIG. 5 is a schematic illustration of a robotic surgical system including a robotic surgical assembly in accordance with the present disclosure.
Figure 6:
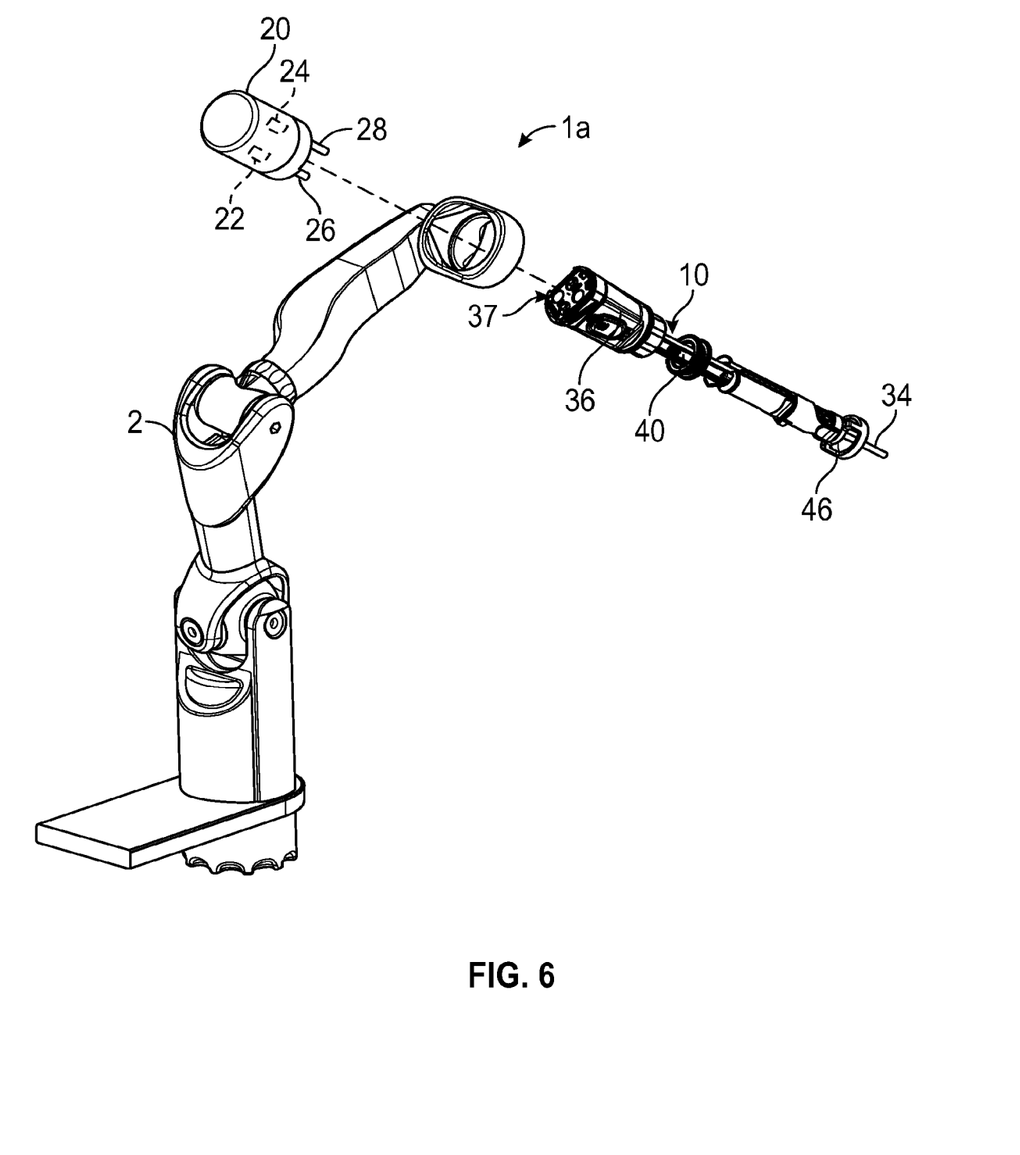
FIG. 6 is a perspective view illustrating a surgical robotic arm, an instrument drive unit, and a uterine manipulator usable with the robotic surgical assembly of FIG. 5.

Referring to FIGS. 5 and 6, a surgical system, such as, for example, a robotic surgical system 1, generally includes a plurality of surgical robotic arms 2, 3 having an instrument drive unit 20 removably attached thereto; a control device 4; and an operating console 5 coupled to the control device 4. A uterine manipulator 10 is removably attached the instrument drive unit 20. As noted above, uterine manipulator 10 may be any of uterine manipulators 100, 200, 300, 400 described above (see FIGS. 1A-4B). The uterine manipulator 10 is configured to be manually operated by a user, to be operably coupled to the instrument drive unit 20 for operation by the robotic surgical system 1, or both. Thus, the uterine manipulator 10, whether being operated manually or via a robotic surgical system 1, may be inserted into a vaginal cavity for use in female pelvic surgical procedures, such as a hysterectomy.

With continued reference to FIG. 5, the operating console 5 includes a display device 6, which is set up in particular to display three-dimensional images, and manual input devices 7, 8, by means of which a person (not shown), for example a surgeon, is able to telemanipulate the robotic arms 2, 3 in a first operating mode, as known in principle to a person skilled in the art. Each of the robotic arms 2, 3 may include a plurality of members, which are connected through joints. The robotic arms 2, 3 may be driven by electric drives (not shown) that are connected to the control device 4. The control device 4 (e.g., a computer) is set up to activate the drives, in particular by means of a computer program, in such a way that the robotic arms 2, 3, their instrument drive units 20, and thus the uterine manipulators 10 execute a desired movement according to a movement defined by means of the manual input devices 7, 8. The control device 4 may also be set up in such a way that it regulates the movement of the robotic arms 2, 3 and/or of the drives.

The robotic surgical system 1 is configured for use on a patient "P" lying on a surgical table "ST" to be treated in a minimally invasive manner by means of a surgical instrument, e.g., the uterine manipulator 10. The robotic surgical system 1 may also include more than two robotic arms 2, 3, the additional robotic arms likewise being connected to the control device 4 and being telemanipulatable by means of the operating console 5. A surgical instrument, for example, the uterine manipulator 10, may also be attached to the additional robotic arm.

The control device 4 may control a plurality of motors (Motor 1 . . . n) with each motor configured to drive a relative rotation of driven members of the uterine manipulator 10 to effect operation and/or movement of components of the uterine manipulator 10. It is contemplated that the control device 4 coordinates the activation of the various motors (Motor 1 . . . n) to coordinate a clockwise or counter-clockwise rotation of drive members of the instrument drive unit 20 in order to coordinate an operation and/or movement of a respective driven member of the uterine manipulator 10.

With specific reference to FIG. 6, the robotic surgical system 1 includes a surgical robotic assembly 1a, which includes the robotic arm 2, the instrument drive unit 20 configured to be coupled to the robotic arm 2, and the uterine manipulator 10 configured to be coupled to the instrument drive unit 20. The instrument drive unit 20 is configured for powering the uterine manipulator 10 and to transfer power and actuation forces from its motors 22, 24 to driven members 30, 32 (FIG. 7) of the uterine manipulator 10 to ultimately drive movement of components of the uterine manipulator 10, for example, an articulation of a tip member 34 of the uterine manipulator 10. The instrument drive unit 20 includes first and second drive members 26, 28 drivingly coupled to a respective motor 22, 24, such that the drive members 26, 28 are independently rotatable with respect to one another.

With reference to FIGS. 7-10, the articulation assembly 38 is partially disposed within the housing 36 and includes first and second driven members 30, 32 supported in the housing 36, first and second nuts 48, 50 operably coupled to the respective first and second driven members 30, 32, and first and second cables 52, 54 coupled to the respective first and second nuts 48, 50. The first and second driven members 30, 32 may be configured as lead screws having an external threading 53 disposed along their length. Each of the first and second driven members 30, 32 are parallel with, and offset from, a longitudinal axis defined by the shaft and has a proximal end portion 30a, 32a, and a distal end portion 30b, 32b. The proximal end portion 30a, 32a of each of the driven members 30, 32 has an input coupler 56, 57 (e.g., crossed protrusion) configured to be non-rotatably coupled to a corresponding output coupler of the respective first and second drive members 26, 28 (FIG. 6) of the instrument drive unit 20. As such, when the instrument drive unit 20 is operably coupled to the housing 36 of the uterine manipulator 10, an actuation of the first and second motors 22, 24 of the instrument drive unit 20 drives a rotation of the first and second driven members 30, 32 of the articulation assembly 38.

Figure 7:
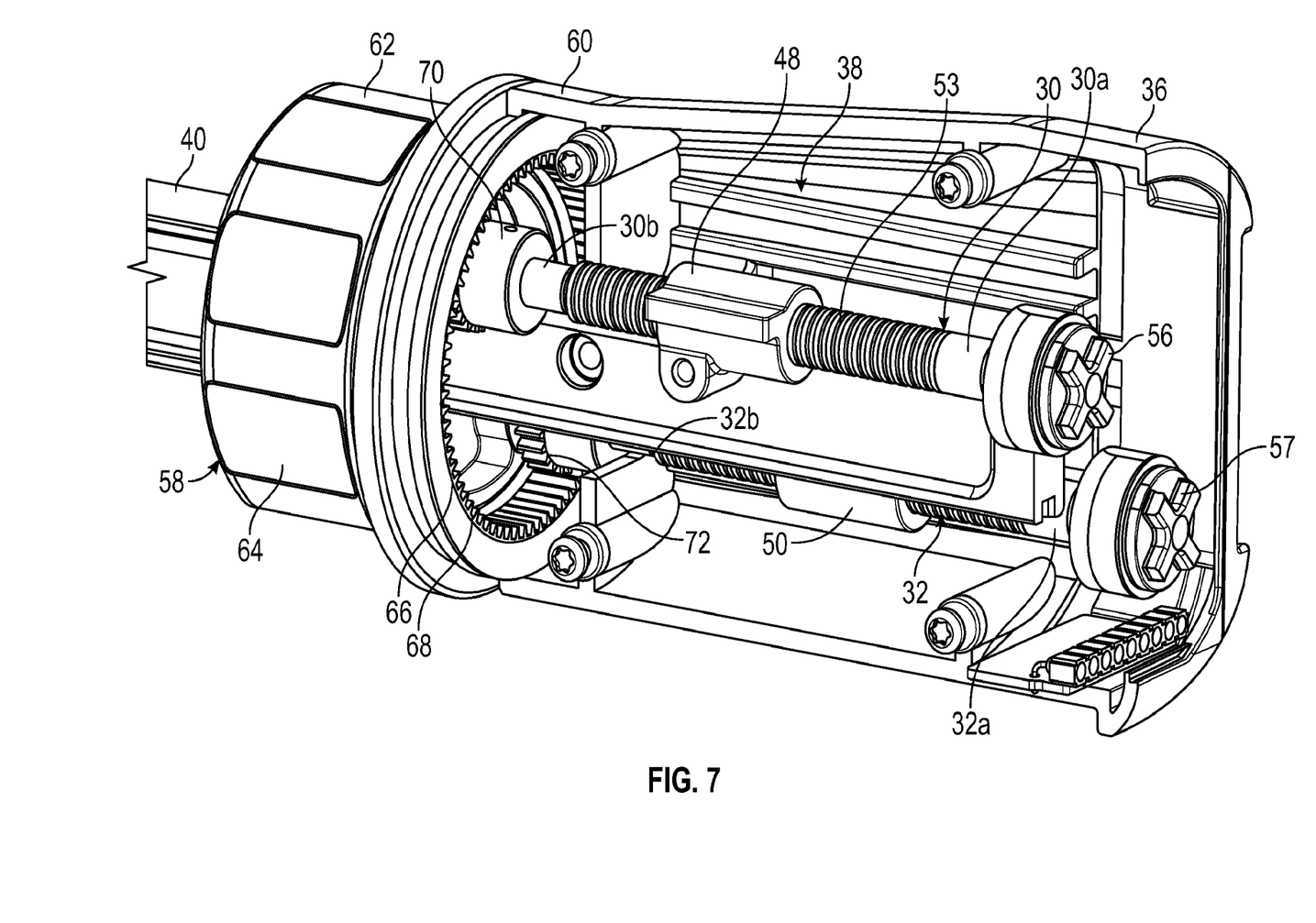
FIG. 7 is a cutaway view illustrating components of an example articulation assembly of the uterine manipulator of FIG. 6.
Figure 8:
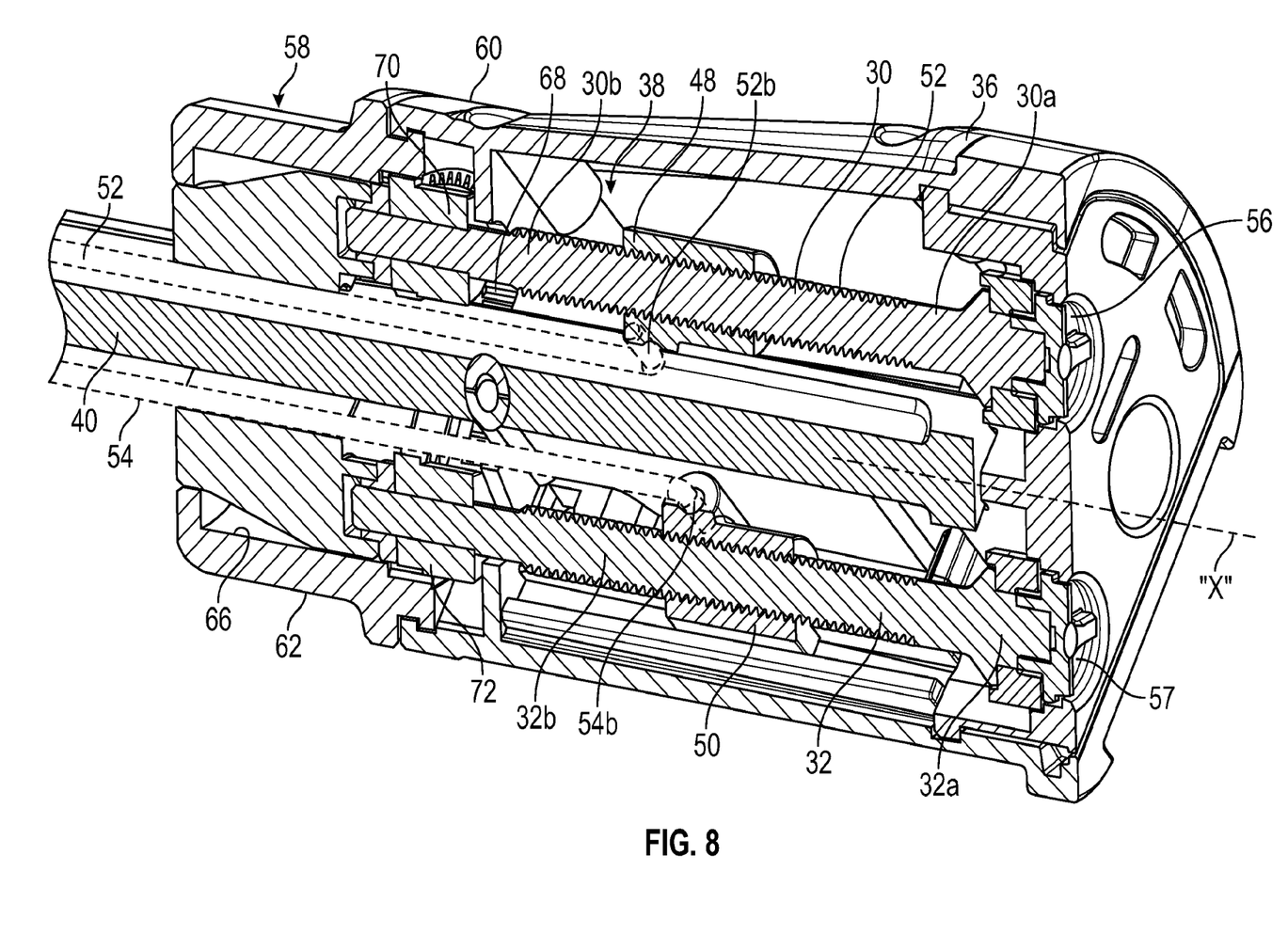
FIG. 8 is a longitudinal cross-sectional view illustrating components of the articulation assembly of FIG. 7.

The uterine manipulator 10 may include a manually-rotatable collar 58 rotatably coupled to a distal end portion 60 of the housing 36 and disposed about the shaft 40. The collar 58 has an outer peripheral surface 62 defining a plurality of surface features 64 configured to assist a clinician in grasping the collar 58. An inner periphery 66 of the collar 58 defines a plurality of gear teeth 68 disposed in a circular array around the shaft 40. The distal end portion 32b of each of the first and second driven members 30, 32 has a gear 70, 72, such as, for example, a spur gear, attached thereto in meshing engagement with the gear teeth 68 of the collar 58. In aspects, the spur gears 70, 72 may be operably coupled to the gear teeth 68 of the collar 58 via an intermediary gear. In other embodiments, the distal end portion 30b, 32b of each of the first and second driven members 30, 32 may be operably coupled to the collar 58 via any suitable mechanism, such as, for example, frictional engagement.

Due to the engagement between the first and second driven members 30, 32 and the collar 58, a manual rotation of the collar 58 results in a rotation of the first and second driven members 30, 32 about their respective longitudinal axes. It is contemplated that the collar 58 may be used in the instance that the instrument drive unit 20 is not attached to the uterine manipulator 10, if power is otherwise not available, and/or if additional manual force is desired.

The first and second nuts 48, 50 of the articulation assembly 38 are threadedly coupled to the threading 53 defined along the respective first and second driven members 30, 32. Each of the first and second nuts 48, 50 may be rotationally restrained by an internal structure of the housing 36 so that rotation of the first and second driven members 30, 32 results in only axial motion of the first and second nuts 48, 50 along the first and second driven members 30, 32.

Figure 10:
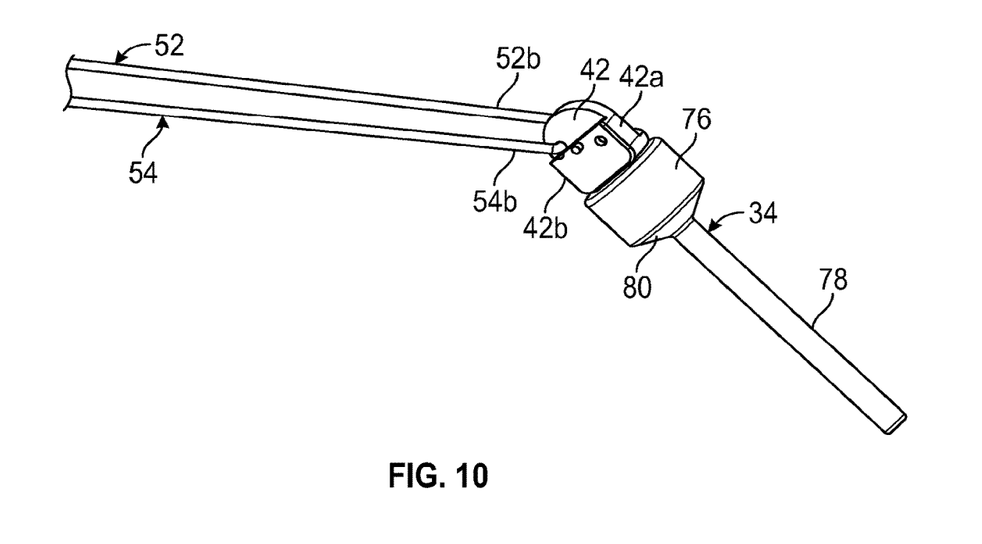
FIG. 10 is a side perspective view, with parts removed, of the distal portion of the uterine manipulator of FIG. 6.

The first and second cables 52, 54 of the articulation assembly 38 are rigid and maintain a linear shape during actuation of the articulation assembly 38. In some aspects, the cables 52, 54 may be fabricated from a flexible material. The cables 52, 54 each have a proximal end portion 52*a*, 54*a* disposed within the housing 36, and a distal end portion 52*b*, 54*b* (FIG. 10). The proximal end portion 52*a*, 54*a* of each of the cables 52, 54 is fixed to the respective first and second nuts 48, 50 via a pin-slot engagement. In other aspects, the proximal end portion 52*a*, 54*a* of each of the cables 52, 54 may be fixed, either directly or indirectly, to the respective first and second nuts 48, 50 via any suitable fastening engagement, such as, for example, adhesives, screws, rivets, knots, or the like.

As best shown in FIG. 10, the distal end portion 52*b* of the first cable 52 is fixed to a first side 42*a* of the tip hub 42, and the distal end portion 54*b* of the second cable 54 is fixed to a second side 42*b* of the tip hub 42. In this way, a translation of the first cable 52 in a first direction (e.g., a distal direction) coupled with a translation of the second cable 54 in a second direction (e.g., a proximal direction), opposite the first direction, causes an articulation of the tip hub 42, along with the tip member 34, relative to the shaft 40. Although shown as pivotable along a single axis, it is contemplated that distal portion of shaft 40 may include articulation links thereby enabling pivoting or articulation of the tip hub 42 relative to the shaft 40 about multiple pivot axes.

Figure 9:
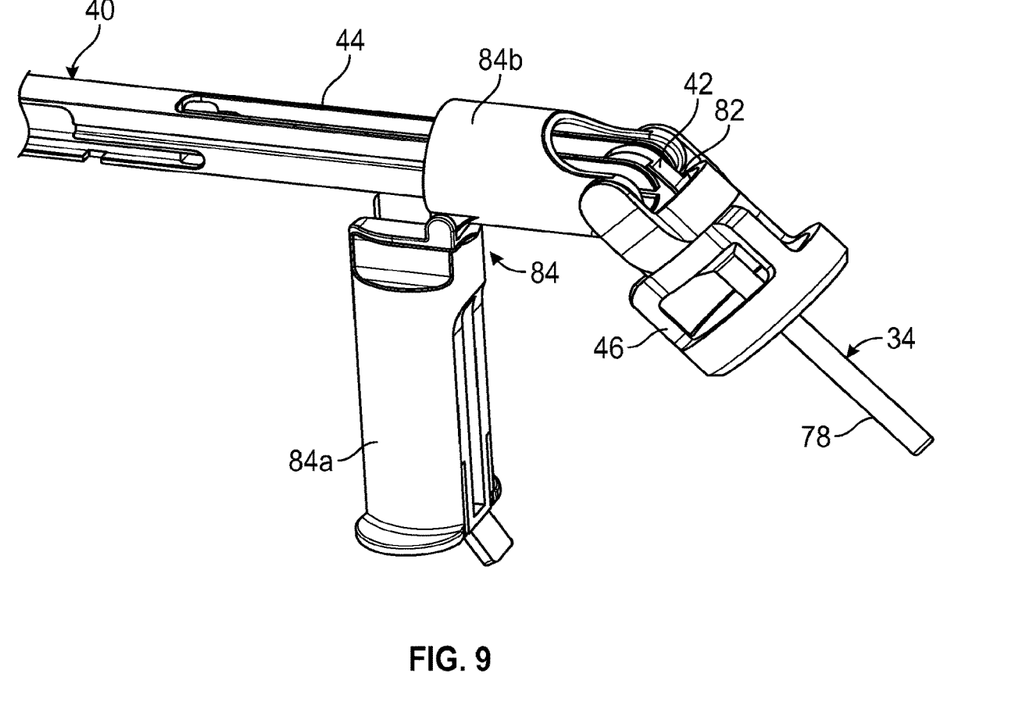
FIG. 9 is a side, perspective view of a distal portion of the uterine manipulator of FIG. 6.

The tip member 34 of the uterine manipulator 10 is attached to the tip hub 42 and has a head portion 76 and an elongate rod 78 extending distally from the head portion 76. In aspects, the tip member 34 may be monolithically formed with the tip hub 42. The head portion 76 may have a distally-facing surface 80 having a frustoconical shape configured to engage the external surface of a cervix. The elongate rod 78 of the tip member 34 may have an elongated, expandable balloon (not shown) for engaging a cervical canal to aid in repositioning of a uterus. The balloon may have a supply line (not shown) extending therefrom configured to be coupled to a source of fluid (e.g., gas or liquid) to selectively expand the balloon. The supply line may be an internal lumen, or multiple internal lumens, extending through an interior of the shaft 40. Alternatively, the supply line may be one or more external lumens extending along an outer surface of the shaft 40.

The cervical cup 46 of the uterine manipulator 10 is configured to capture a cervix therein and is pivotably coupled to the distal end portion 44 of the shaft 40. The head portion 76 of the tip member 34 is received in an opening 82 defined in the cervical cup 46, which is sized to capture the head portion 76 therein, such that the tip member 34 and the cervical cup 46 articulate together as one unit. The elongate rod 78 of the tip member 34 extends distally from the cervical cup 46 and is centrally disposed therein. The cervical cup 46 may be pivotably coupled to a sleeve 84 that is slidably disposed about and detachably coupled to the shaft 40.

The sleeve 84 includes a distal portion 84*b* and a proximal portion 84*a* pivotably coupled to the distal portion 84*b*. The distal portion 84*b* of the sleeve 84 is slidable along and relative to the shaft 40 to position the cervical cup 46 about the tip member 34 when ready for use. Upon positioning the distal portion 84*b* of the sleeve 84 and the attached cervical cup 46 in an in-use position (FIG. 9), the proximal portion 84*a* of the sleeve 84 may be pivoted from a first state (FIG. 9), in which the proximal portion 84*a* is disconnected from the shaft 40, to a second state (FIG. 6), in which the proximal portion 84*a* is aligned with the distal portion 84*b* and is connected to the shaft 40. In the second state, the sleeve 84 and the cervical cup 46 are axially fixed to the shaft 40. It is contemplated that the proximal portion 84*a* of the sleeve 84 may be releasably engaged to the shaft 40 via a friction fit engagement or any suitable fastening engagement.

The sleeve 84 may have a vaginal occluder balloon (not shown) disposed about the distal portion 84*b* thereof. The vaginal occluder balloon is expandable within the vagina to facilitate securing the uterine manipulator in a selected position relative to the uterus. The vaginal occluder balloon may have a supply line (not shown) extending therefrom configured to be coupled to a source of fluid (e.g., gas or liquid) for selectively expanding the vaginal occluder balloon. The supply line may be an internal lumen, or multiple internal lumens, extending through an interior of the shaft 40. Alternatively, the supply line may be one or more external lumens extending along an outer surface of the shaft 40.

In operation, a hysterectomy or other uterine manipulation procedure may be performed utilizing the uterine manipulator 10 of the present disclosure. During, or in preparation for, the procedure, the uterine manipulator 10 is either, or both, manually operated by a user and/or coupled to the robotic arm 2 and an instrument drive unit 20. Upon coupling the uterine manipulator 10 to the instrument drive unit 20, the drive members 26, 28 of the instrument drive unit 20 are operably coupled with the first and second driven members 30, 32 of the uterine manipulator 10.

To robotically articulate the tip member 34 of the uterine manipulator 10, the first and second motors 22, 24 of the instrument drive unit 20 are actuated, whereby the first and second drive members 22, 24 rotate in opposite directions to rotate the first and second driven members 32 of the uterine manipulator 10 in opposite directions. In some aspects, instead of rotating the first and second driven members 30, 32 in opposite directions, the first and second driven members 30, 32 may have opposite thread handedness, e.g., the first driven member 30 may have a right-handed thread whereas the second driven member 32 may have a left-handed thread.

Since the first and second nuts 48, 50 are threadedly coupled to the first and second driven members 30, 32, rotation of the first and second driven members 30, 32 drive a translation of the first and second nuts 48, 50 along the respective first and second driven members 30, 32 in opposite directions from one another. For example, the first nut 48 may translate distally whereas the second nut 50 may translate proximally. As the first nut 48 translates distally, so does the first cable 52, and as the second nut 50 translates proximally, so does the second cable 54. Due to the distal end portion 52*b*, 54*b* of the first and second cables 52, 54 being fixed to opposing sides 42*a*, 42*b* of the pivot hub 42/tip member 34, the tip member 34 articulates relative to the distal end portion 44 of the shaft 40. When the tip member 34 is disposed within a uterus, articulation of the tip member 34 functions to manipulate the uterus and maintain the uterus in a selected position. Manual articulation of the tip member 34 of the uterine manipulator 10 may be accomplished via rotation of rotatable collar 58 in either direction to likewise drive a translation of the first and second nuts 48, 50 along the respective first and second driven members 30, 32 in opposite directions from one another, as detailed above.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A uterine manipulator, comprising:
a housing;
a shaft extending distally from the housing;
a tip hub pivotably coupled to a distal end portion of the shaft;
an articulation assembly disposed within the housing and including a drive cable operably coupled to the tip hub, the drive cable configured to pivot the tip hub relative to the shaft upon actuation of the articulation assembly; and
a handle pivotably coupled to the housing and movable between an unfolded configuration and a folded configuration to facilitate storage of the handle within a recess defined in the housing such that the handle can be selectively folded in the recess in a non-protruding manner relative to the housing, the handle operably coupled to the drive cable, the handle configured to be manually gripped by a user in the unfolded configuration and rotated radially relative to the housing which, in turn, correspondingly articulates the tip hub relative to the shaft.

2. The uterine manipulator according to claim 1, wherein the handle extends outward from a proximal portion of the housing and is permanently coupled to the housing.

3. The uterine manipulator according to claim 1, wherein the handle includes a coupling member operably engaged between the handle and the housing, the coupling member removably couplable to a proximal portion of the housing and configured to releasably couple the handle to the housing.

4. The uterine manipulator according to claim 1, wherein the handle is pivotable between the unfolded configuration, where the handle extends substantially perpendicular relative to a surface of the housing, and a folded configuration, where the handle extends substantially parallel along a surface of the housing.

5. The uterine manipulator according to claim 1, wherein the shaft is detachable from the housing and the handle is operably coupled to the shaft.

6. The uterine manipulator according to claim 1, wherein at least a distal portion of the shaft is curved.

7. The uterine manipulator according to claim 1, wherein the shaft defines an internal lumen extending along a length of the shaft.

8. A uterine manipulator, comprising:
a housing;
a shaft extending distally from the housing;
a tip hub pivotably coupled to a distal end portion of the shaft;
an articulation assembly disposed within the housing and including a first drive cable operably coupled to the tip hub, the first drive cable actuatable manually by a user or robotically by a robot surgical system to pivot the tip hub relative to the shaft upon actuation of the articulation assembly;
a handle pivotably coupled to the housing and operably coupled to the drive cable, the handle movable between an unfolded configuration and a folded configuration to facilitate storage of the handle within a recess defined in the housing such that the handle can be selectively folded in the recess in a non-protruding manner relative to the housing, the handle configured to be manually gripped by the user to rotate the handle radially relative to the housing to translate the first drive cable and correspondingly articulate the tip hub relative to the shaft; and
a first driven member disposed in the housing and adapted to couple to a first drive member of the robot surgical system, wherein actuation of the first drive member translates the first drive cable to correspondingly articulate the tip hub relative to the shaft.

9. The uterine manipulator according to claim 8, further comprising a rotatable collar operably coupled to the articulation assembly and configured to be manually rotated to correspondingly articulate the tip hub relative to the shaft.

10. The uterine manipulator according to claim 8, wherein the articulation assembly includes a second driven member disposed in the housing and adapted to couple to a second drive member of the robot surgical system, wherein actuation of the second drive member translates a second drive cable to correspondingly articulate the tip hub relative to the shaft.

11. The uterine manipulator according to claim 10, wherein a distal end portion of the first drive cable is coupled to a first side of the tip hub and a distal end portion of the second drive cable is coupled to a second side of the tip hub and wherein actuation of the first drive member to translate the first drive cable moves the tip hub in a first direction relative to the shaft and actuation of the second drive member to translate the second drive cable moves the tip hub in a second direction relative to the shaft.

* * * * *